United States Patent [19]

Akhavi

[11] 4,240,424
[45] Dec. 23, 1980

[54] SYRINGE LOCKING SLEEVE

[75] Inventor: David S. Akhavi, Los Angeles, Calif.

[73] Assignee: American Hospital Supply Corporation, Evanston, Ill.

[21] Appl. No.: 953,607

[22] Filed: Oct. 23, 1978

[51] Int. Cl.³ .............................................. A61M 5/00
[52] U.S. Cl. ............................. 128/218 R; 128/218 N
[58] Field of Search ....... 128/218 R, 218 N, 218 NV, 128/215, 216, 221, 220

[56] References Cited

U.S. PATENT DOCUMENTS

| 3,542,024 | 11/1970 | Burke | 128/221 |
| 3,728,184 | 4/1973 | Burke | 128/218 R UX |
| 4,027,669 | 6/1977 | Johnson et al. | 128/218 N |

FOREIGN PATENT DOCUMENTS 1086763  10/1967  United Kingdom ................ 128/221 X Primary Examiner—John D. Yasko
Attorney, Agent, or Firm—Larry N. Barger

[57] ABSTRACT

A syringe barrel with an integral laterally flexible locking sleeve with peripheral segmenting slots and a series of integral longitudinal spring ribs on an outer surface of the flexible sleeve.

9 Claims, 3 Drawing Figures

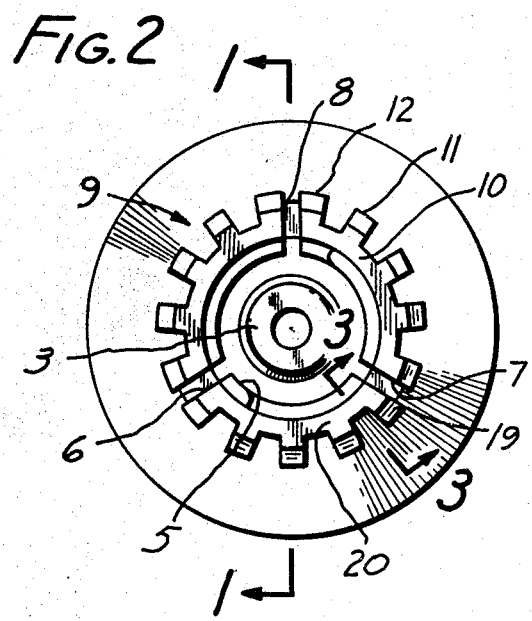
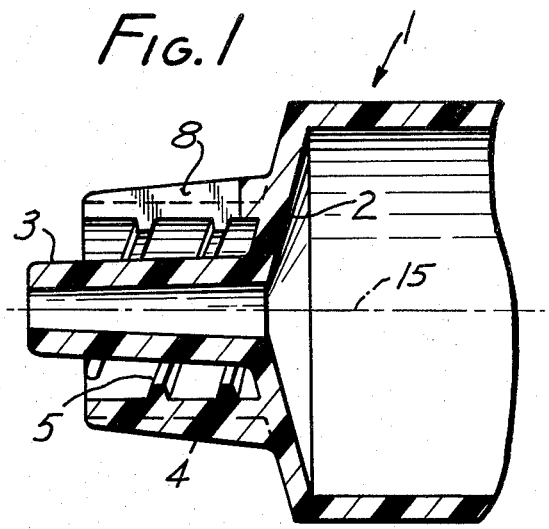
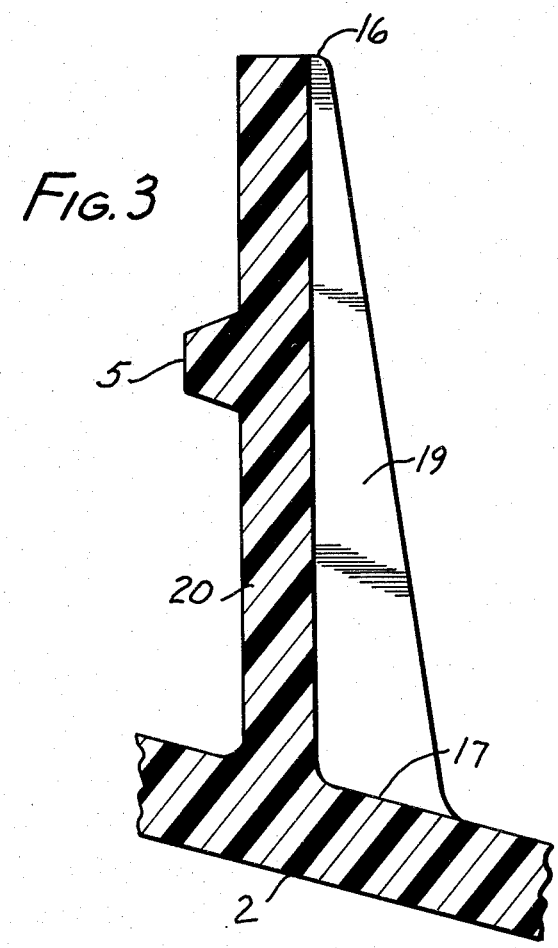

SYRINGE LOCKING SLEEVE

BACKGROUND

U.S. Pat. No. 4,027,669 describes a thermoplastic syringe barrel with an integral thermoplastic sleeve that is internally threaded for aiding and holding a needle or the like to a tapered adapter of the barrel. Circumferentially spaced slots in the sleeve permit the sleeve to flex outwardly during its moulding process for longitudinally stripping the sleeve from its mold without requiring expensive unscrewing machinery. This strip ejection process for the nonslotted sleeve is described in British Pat. No. 1,086,763 (U.S. Pat. No. 3,402,713).

Separately formed locking sleeves, which were subsequently bonded to the syringe barrel and were not laterally flexible for strip mold ejection, sometimes included external grooves for registering with the expensive unscrewing mechanism on the molding machine, as shown in U.S. Pat. No. 3,542,024. It is also an expensive process to subsequently bond the locking sleeve to the syringe barrel.

The integral thermoplastic retention sleeves must be sufficiently flexible for longitudinally stripping from the molding die without substantially distorting the internal threads. The sleeve must also have sufficient resistance against outward flexibility to prevent flanges or ears of a needle from stripping out of the sleeve's threads. To insure this latter feature, the sleeve of U.S. Pat. No. 4,024,669 had to be made with a thick wall section; i.e., approximately 0.050 inch. Such wall thickness in the sleeve was at the borderline of flexing sufficiently for mold removal, but still stiff enough for hypodermic needle retention. Because of this thick wall section, the molding cycles had to be relatively long for the plastic to cool in the collar prior to ejection, thus increasing manufacturing costs.

SUMMARY OF THE INVENTION

The present invention overcomes the above problems by providing a very thin flexible thread supporting inner section of the sleeve which is easy to eject from the mold. This thin inner section is backed up by a series of longitudinally extending thermoplastic spring ribs that are integrally formed with the barrel and inner section of the sleeve. These spring ribs help stiffen the sleeve for retaining a hypodermic needle, but still permit easy strip ejection from the mold. This construction also substantially shortens molding cycle time.

THE DRAWINGS

FIG. 1 is a sectional view of a forward portion of a syringe barrel taken along line 1—1 of FIG. 2;

FIG. 2 is a left-hand view of FIG. 1; and

FIG. 3 is an enlarged sectional view taken along line 3—3 of FIG. 2.

DETAILED DESCRIPTION

In FIG. 1, a syringe barrel 1 is shown with a front wall 2 that is connected to an externally tapered needle adapter 3. Surrounding needle adapter 3 is a retention sleeve 4 with internal threads 5. As seen in FIG. 1, all of the above listed components are formed as a unitary one-piece construction. Preferably the syringe barrel, including the above components, is injection molded of a polypropylene thermoplastic material.

In FIG. 2, it is seen that the retention sleeve is segmented into three sections by slots 6, 7, and 8. These slots help the segments, such as 9, to flex outwardly during strip ejection from a mold. In addition to threads 5, each segment of the needle locking collar includes a thin flexible section 10 which preferably has a thickness of from 0.020 to 0.040 inch. Backing up this thin inner section 10 are a series of spring ribs 11 and 12 which are of a thermoplastic material and integrally formed with inner section 10. These spring ribs are longitudinally oriented parallel to a longitudinal axis 15 of the syringe barrel.

An improvement to the slot construction is described in a co-pending application entitled, "Segmented Syringe Locking Sleeve", Ser. No. 953,689, filed Oct. 23, 1975.

As shown in FIG. 3, each spring rib has a forward end 16 adjacent a forward end of the locking sleeve and a rear end 17 which is integrally formed with front wall 2 of the syringe barrel. The particular rib in FIG. 3, designated as 19, is substantially thinner at its forward end 16 than at its rearward end 17 in a direction extending outwardly from the thin flexible section 10. Preferably the spring rib 19 tapers between its two ends. It has been found that such combination of spring rib and thin inner section, shown as 20 on the particular segment in FIG. 3, provides very good lateral flexibility for mold ejection, and excellent backup stiffness for retaining a hypodermic needle by threads 5. The construction shown in the attached figures also has as an added advantage of very fast and economical cycling times in the mold.

In the above description, a specific example has been used to describe the invention. However, it is understood by those skilled in the art that certain modifications can be made to this example without departing from the spirit and scope of the invention.

I claim:

1. A thermoplastic syringe barrel with an integral laterally flexible thermoplastic locking member having a longitudinal axis, wherein the improvement comprises: an inner retention portion of the locking member for securing a needle or the like to the barrel; and at least one longitudinally extending outer spring rib integral with the retention portion said rib adapted to flex outwardly during strip ejection and without unscrewing during the molding process.

2. A syringe as set forth in claim 1, wherein the locking member is a sleeve with at least one longitudinal slot peripherally segmenting the sleeve.

3. A syringe as set forth in claim 1, wherein there are a series of longitudinally extending spring ribs.

4. A syringe as set forth in claim 1, wherein the spring rib has a rear end joined to the barrel and a forward end spaced from the barrel.

5. A syringe as set forth in claim 1, wherein the barrel and locking member's inner retention portion and spring rib are of one-piece polypropylene.

6. A syringe as set forth in claim 1, wherein the locking member is a peripherally segmented sleeve having integral internal thermoplastic threads.

7. A medical device with a thermoplastic locking sleeve having a longitudinal axis and being integrally formed with and surrounding a hollow adapter, wherein the improvement comprises: an inner retention portion of the sleeve; and at least one longitudinally extending outer spring rib integral with the retention portion said rib adapted to flex outwardly during strip ejection and without unscrewing during the molding process.

8. A thermoplastic syringe barrel with an integral laterally flexible thermoplastic locking member, wherein the improvement comprises: an inner retention portion of the locking member for securing a needle or the like to the barrel; at least one outer spring rib integral with these retention portions; said spring rib having a rear end joined to the barrel and a forward end spaced from the barrel; and this rib is substantially thicker at its rear end than at its forward end said rib adapted to flex outwardly during strip ejection and without unscrewing during the molding process.

9. A syringe as set forth in claim 8, wherein the rib progressively tapers from its rear end towards its forward end.

* * * * *